(12) United States Patent
Kessler et al.

(10) Patent No.: US 6,328,038 B1
(45) Date of Patent: Dec. 11, 2001

(54) NASAL CANNULA RETAINER

(76) Inventors: Fred Bruce Kessler, 25123 Margot Ct., Beachwood, OH (US) 44122; David Michael Berzon, 2513 Ginger Wren, Pepper Pike, OH (US) 44124

(*) Notice: Subject to any disclaimer, the term of this patent is extended or adjusted under 35 U.S.C. 154(b) by 0 days.

(21) Appl. No.: 09/114,988

(22) Filed: Jul. 14, 1998

(51) Int. Cl.[7] .................................................. A61M 15/08
(52) U.S. Cl. ............................. 128/207.18; 128/207.17; 128/200.25; 128/201.18
(58) Field of Search ...................... 128/207.18, 207.17, 128/200.26, 201.182, 203.22, 204.12, DIG. 26, 204.11; 604/94, 174

(56) References Cited

U.S. PATENT DOCUMENTS

| | | |
|---|---|---|
| D. 243,477 | 2/1977 | Cutruzzula et al. . |
| D. 375,355 | 11/1996 | Bierman . |
| D. 375,356 | 11/1996 | Bierman . |
| D. 377,831 | 2/1997 | Bierman . |
| 3,046,989 | 7/1962 | Hill . |
| 3,288,136 | 11/1966 | Lund . |
| 3,430,300 | 3/1969 | Doan . |
| 3,682,171 | 8/1972 | Dali et al. . |
| 4,120,304 | 10/1978 | Moor . |
| 4,142,527 * | 3/1979 | Garcia ........................ 128/DIG. 26 |
| 4,324,236 | 4/1982 | Gordon et al. . |
| 4,454,880 | 6/1984 | Muto et al. . |
| 4,480,639 * | 11/1984 | Peterson et al. ................ 128/207.18 |
| 4,490,141 | 12/1984 | Lacko et al. . |
| 4,498,903 * | 2/1985 | Mathew ............................. 604/174 |
| 4,534,762 | 8/1985 | Heyer . |
| 4,738,662 | 4/1988 | Kalt et al. . |
| 4,742,824 * | 5/1988 | Payton et al. .................. 128/DIG. 26 |
| 4,774,946 * | 10/1988 | Ackerman et al. ............. 128/207.18 |
| 4,804,374 | 2/1989 | Laskody . |
| 4,823,789 | 4/1989 | Beisang, III . |
| 4,932,943 | 6/1990 | Nowak . |
| 5,117,818 * | 6/1992 | Palfy .............................. 128/204.11 |
| 5,135,506 | 8/1992 | Gentelia et al. . |
| 5,156,641 | 10/1992 | White . |
| 5,172,688 | 12/1992 | Dillon . |

(List continued on next page.)

FOREIGN PATENT DOCUMENTS

| | | |
|---|---|---|
| 503739 | 6/1954 | (CA) . |
| 2251796 | 7/1992 | (GB) . |
| 9610435 | 4/1996 | (WO) . |
| 9715337 | 5/1997 | (WO) . |
| 9715342 | 5/1997 | (WO) . |

OTHER PUBLICATIONS

Breathe Right® nasal strips/10 Most Commonly Asked Questions About Breathe Right® nasal strips/ Apr. 23, 1998/ pp. 1–2.

So Science Proves That Breathe Right Nasal Strips Work. But How?/ Apr. 23, 1998/ pp. 1–2.

Statlock Securement Devices/ The Science of Securement/ pp. 1–12.

*Primary Examiner*—John G. Weiss
*Assistant Examiner*—V. Srivastava
(74) *Attorney, Agent, or Firm*—Renner, Otto, Boisselle & Sklar, LLP

(57) ABSTRACT

A nasal cannula retainer has a flexible member and cannula grips. The flexible member has a central nose portion with an adhesive backing for adhering to a patient's nose and two cheek portions connected to the nose portion, each of the cheek portions having an adhesive backing for adhering to a patient's cheek. The adhesive layers are covered with a peel layer which is removed prior to applying the retainer. The cannula grips are attached to the cheek portions to secure a nasal cannula on each of the patient's cheeks. The grips are releasable and reusable, allowing the cannula to be repositioned or temporarily removed without the need for the retainer to be discarded and replaced, and without the use of tape to secure the cannula to the retainer after the cannula is repositioned.

13 Claims, 4 Drawing Sheets

U.S. PATENT DOCUMENTS

| | | | |
|---|---|---|---|
| 5,192,273 | | 3/1993 | Bierman et al. . |
| 5,192,274 | | 3/1993 | Bierman . |
| 5,295,480 | * | 3/1994 | Zeme .................... 128/207.17 |
| 5,308,339 | | 5/1994 | Kalt et al. . |
| 5,314,411 | | 5/1994 | Bierman et al. . |
| 5,354,282 | | 10/1994 | Bierman . |
| 5,438,979 | * | 8/1995 | Johnson, Jr. et al. .......... 128/207.18 |
| 5,456,671 | | 10/1995 | Bierman . |
| 5,488,944 | * | 2/1996 | Kennedy .................... 128/202.18 |
| 5,509,409 | * | 4/1996 | Weatherholt .................... 128/207.18 |
| 5,513,635 | * | 5/1996 | Bedi .................... 128/207.18 |
| 5,526,806 | * | 6/1996 | Tansoni .................... 128/207.18 |
| 5,533,506 | * | 7/1996 | Wood .................... 128/207.18 |
| 5,578,013 | | 11/1996 | Bierman . |
| 5,637,098 | | 6/1997 | Bierman . |
| 5,645,058 | * | 7/1997 | Odum .................... 128/207.18 |
| 5,674,202 | * | 10/1997 | Atallah .................... 604/174 |
| 5,682,881 | * | 11/1997 | Winthrop et al. .................... 128/207.18 |
| 5,752,511 | * | 5/1998 | Simmons et al. .................... 128/207.18 |

* cited by examiner

NASAL CANNULA RETAINER

FIELD OF THE INVENTION

The invention is directed to a means for securing nasal cannulae, and more specifically to nasal cannulae which are used to provide oxygen to a patient.

BACKGROUND OF THE INVENTION

Currently nasal cannulae are held in place by routing the cannula tubing over the ears of a patient and retaining them on the patient's head by use of elastic bands. This routing has a disadvantage in that the cannula often becomes dislodged from the patient's nose when the patient moves. In addition, such a routing is uncomfortable for the patient, especially when the cannula must be in place for long periods of time, as is common. For example, the patient's skin may become chafed and irritated by movement of the patient's head, and the cannula may be pulled when the patient moves during sleep.

SUMMARY OF THE INVENTION

A nasal cannula retainer has a flexible member and cannula grips. The flexible member has a central nose portion with an adhesive backing for adhering to a patient's nose and two cheek portions connected to the nose portion, each of the cheek portions having an adhesive backing for adhering to a patient's cheek. The adhesive layers are covered with a peel layer which is removed prior to applying the retainer.

The cannula grips are attached to the cheek portions to secure a nasal cannula on each of the patient's cheeks. The grips are releasable and reusable, allowing the cannula facilely to be repositioned or temporarily removed without the need for the retainer to be discarded and replaced, and without the use of tape to secure the cannula to the retainer after the cannula is repositioned. Since the grips do not use an adhesive, there is no adhesive residue on a repositioned cannula that otherwise might cause the cannula to become dirty or to stick to the patient or to other items.

The nasal cannula retainer of the present invention offers several other advantages over the various prior devices: the cannula grips are securely attached to the patient, better and more securely anchoring the cannula when compared with devices which attach to the cannula by means of flexible tape strips or loops; the cannula grips are attached to the patient's cheeks, where they are close enough to where the cannula enters the patient's nose to minimize the problem of the cannula becoming dislodged from the nose or misaligned relative to the nostril(s) when the patient moves his or her head, and where the retainer does not interfere with the patient's eating or drinking and does not get soiled by eating and drinking; and the flexible member is attached to both the nose and cheeks of the patient, so that any forces tending to pull off the retainer are spread over a large area.

The grips have many possible designs. Some of the possible designs for the grips are enumerated below, although the invention is not limited to these designs.

The grips may be snap-in clips made of a resilient material, each grip having either a single piece or multiple pieces. Such clips may have a semicircular recess conforming to the cannula. Alternatively, the clips may each include a base portion and protrusions attached to the base, the protrusions securing the cannula when it is snapped into the clip.

The grips may be hinged clamps with a releasable locking device, each section of a clamp having a semi-circular recess conforming to the shape of the cannula.

The grips may include a strip or strips made of synthetic material with separable adhering hooks and loops, such as the material sold under the trademark VELCRO.

According to one aspect of the invention, a nasal cannula retainer includes a flexible member for adhering to a patient, and a pair of releasable and reusable grips attached to the flexible member for securing a nasal cannula on opposite sides of a nose of a patient.

According to another aspect of the invention, a method of releasably retaining a nasal cannula includes the steps of adhering a nasal cannula retainer having a pair of releasable and reusable grips to a patient such that the grips are on opposite sides of a nose of the patient, and securing the nasal cannula with the grips.

According to yet another aspect of the invention, a nasal cannula retainer includes a bendable substrate having an adhesive layer thereon for adhering to a patient, and a pair of releasable fasteners attached to the substrate for holding the cannula, the fasteners being on opposite sides of a nose of the patient.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION

Figure 1A:
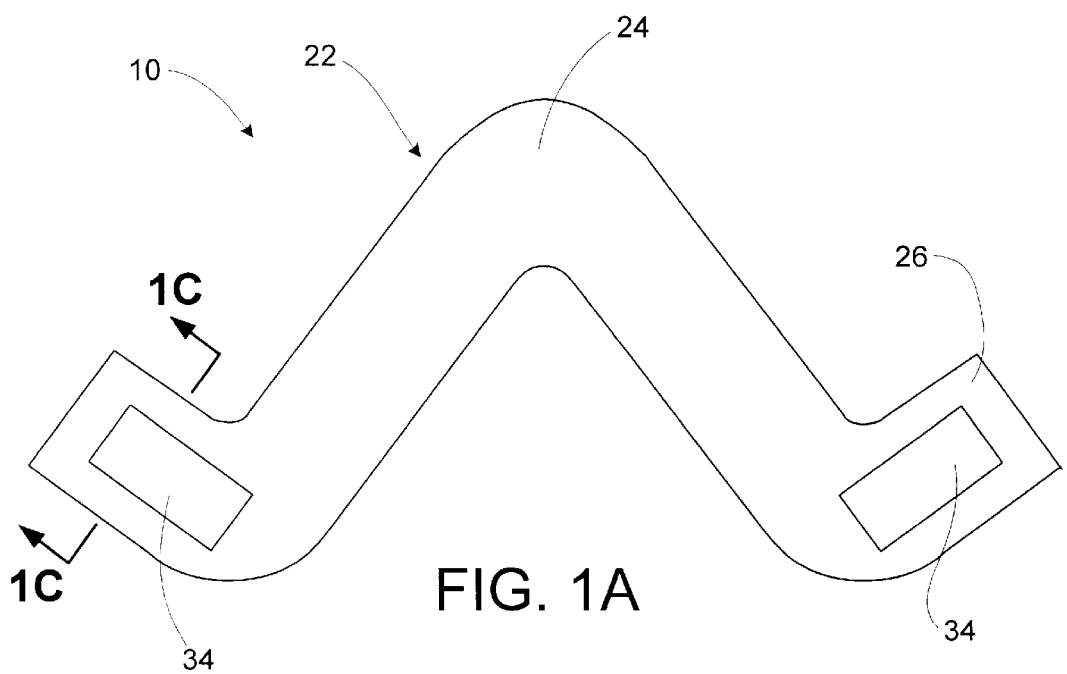
FIGS. 1A and 1B are front and back views, respectively, of a nasal cannula retainer of the present invention.
Figure 1B:
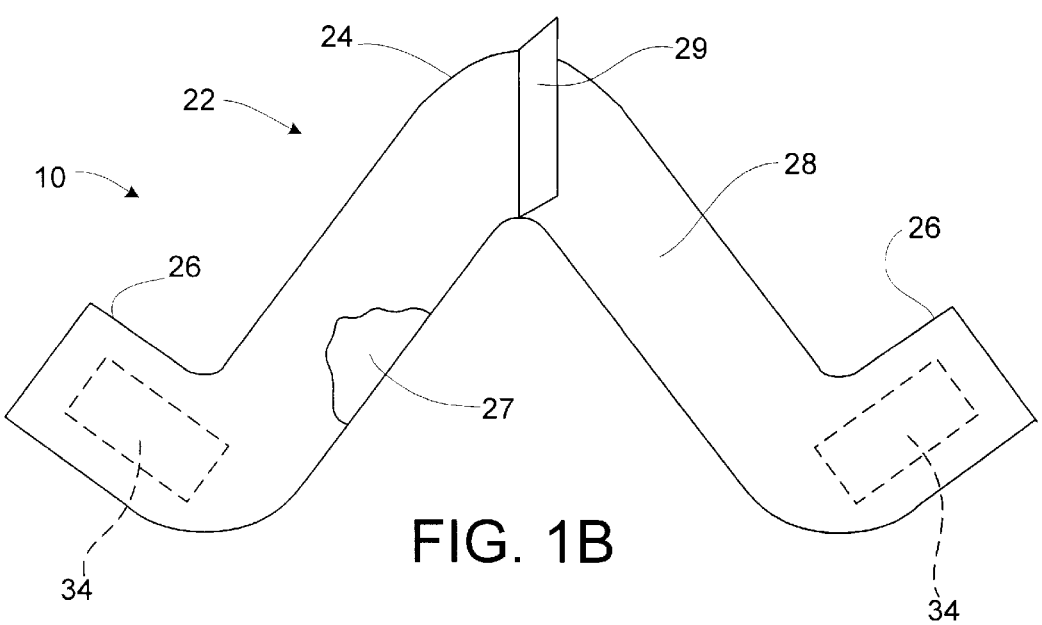

Referring initially to FIGS. 1A–1C and 2, a nasal cannula retainer 10 is used to retain a nasal cannula 12 such that outlet ports 14 of the cannula 12 remain in nostrils 16 of patient 20. The retainer 10 includes a flexible member 22 which has a central nose portion 24 and a pair of cheek portions 26. The member 22 may be made out of materials commonly used for medical devices where skin contact, conformability and flexibility are required. Several non-limiting examples of such material include plastic, cloth or fabric or other materials which can provide the functions requirements described herein.

Figure 2:
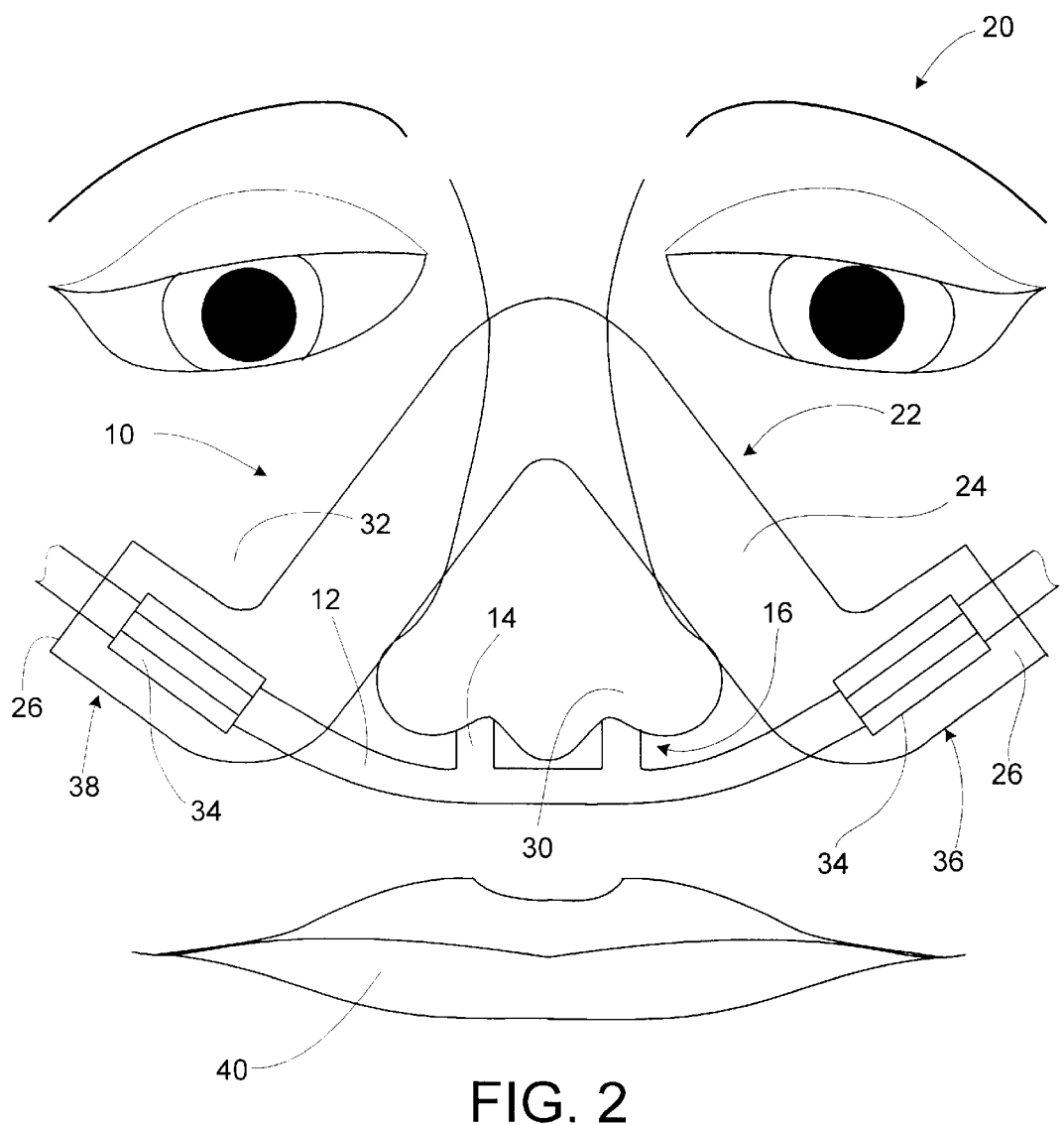
FIG. 2 is plan view of the nasal cannula retainer shown in FIG. 1, securing a cannula in the nostrils of a patient.

The member 22 has an adhesive backing 27, covered prior to use by a peel layer 28. The peel layer 28 is removable from the adhesive backing 27 with the aid of one or more tabs 29 attached to the peel layer 28. The adhesive backing 27 on the member 22 is used to adhere the member 22 to the patient 20. Specifically, the nose portion 24 is adhered to a nose 30 of the patient 20, and the cheek portions 26 are adhered to cheeks 32 of the patient 20. The adhesive material forming the adhesive backing may be located only at selected areas (less than all) of the member 22, examples being at the nose portion 24 and/or at the cheek portions 26. Preferably the adhesive backing is at the nose and cheek portions. If desired, the adhesive backing 27 may cover the entire or substantially the entire surface of the member 22 for adhering the member 22 to the face of a patient, e.g., as is illustrated in FIG. 2.

The retainer 10 has releasable grips 26, schematically illustrated in FIGS. 1A–1C and 2, which are glued or otherwise attached to the cheek portions 26. The grips 34 retain the cannula 12 in two locations 36, 38 on opposite sides of the nose 30. Several grips which may be used in the retainer 10 are described below with respect to several other drawing figures; these are exemplary, and it will be appreciated that other types of grips may be used in accordance with the present invention.

The grips 34 are securely attached to the patient 20 via the cheek portions 26; this provides better anchoring of the cannula 12 when compared with devices which attach a cannula by means of flexible tape strips or loops. Retaining the cannula 12 at locations 36, 38 close to the cheeks 32 of the patient 20 minimizes the problem of the outlet ports 14 becoming dislodged from the nostrils 16 when the patient 20 moves his or her head. Also, locating the flexible member 22 and the grips 34 away from mouth 40 of the patient 20 keeps the retainer 10 from getting soiled when the patient 20 eats or drinks.

The relatively wide extent or area of the retainer 10 provides increased stability when compared with prior art devices. Also, the flexible member 22, being attached to the patient 20 over a large area encompassing parts of both the nose 30 and the cheeks 32, e.g. by the adhesive 27, is well-secured against forces tending to pull away or otherwise to dislodge the retainer 10 from the patient 20.

The grips 34, being releasable and reusable, allow the cannula 12 to be repositioned or temporarily removed without the need for the retainer 10 to be discarded and replaced, and without the use of tape to secure the cannula 12 to the retainer 10 after the cannula 12 is repositioned. Since the grips 34 do not ordinarily require an adhesive to secure them to the cannula 12, there is no adhesive residue on a repositioned or reattached cannula; such adhesive residue might otherwise cause the cannula to become dirty or to stick to the patient or to other items.

Figure 1C:
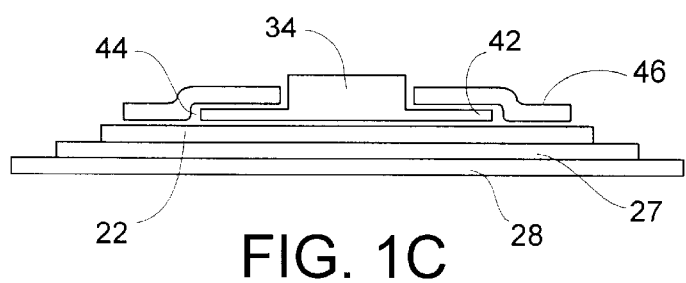
FIG. 1C is a cross-sectional view of a portion of the nasal cannula retainer looking along line 1C—1C of FIG. 1A.

One method of adhering the grips 34 to the flexible member 22 is shown in FIG. 1C. There the grip 34 is shown with a protruding base 42, which is immersed in an adhesive layer 44, and is covered by an upper layer 46 of flexible material. The adhesive of the layer 44 may be the same as that of the backing 27, and the material of the upper layer 46 may be the same as that of the member 22. The adhesive layer 44 holds together the retainer 22, grip 34 (including the protruding base 42) and the layer 46; and the protruding base 42 (e.g., the illustrated extending flange portions thereof) is sandwiched between the retainer 22 and the layer 46 for secure retention and protection of that portion of the base and of the grip itself. It will be appreciated that many other techniques may be used to secure the grips 34 to the flexible member 22.

Figure 3:
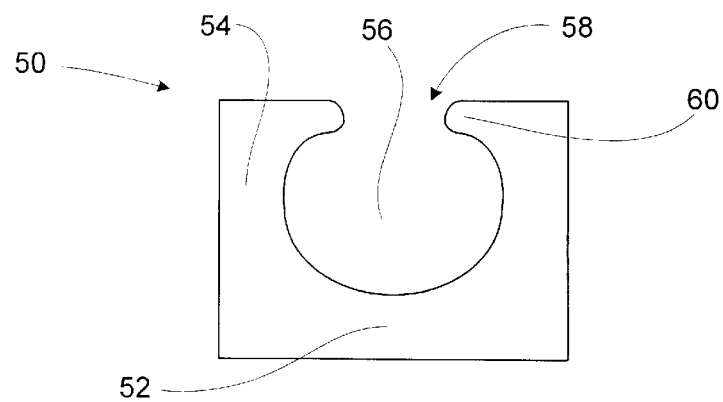
FIG. 3 is a side view of a snap-in clip which may be used for gripping a nasal cannula as part of the retainer of the present invention.

Many possible forms of grip 34 can be employed. One embodiment is a snap-in clip 50 shown in FIG. 3. The clip 50 has a base 52 and a pair of arms 54 extending from the base 52. The base 52 and the arms 54 may be formed as a single piece. The base 52 and the arms 54 cooperate to enclose a recess 56 in the clip 50. The recess 56 has a substantially semi-circular cross-section. The arms 54 are made of a resilient material. For example, the clip 50 may be a molded plastic device. As the cannula 12 is pressed down along the opening 58, the arms 54 flex outward and the cannula 12 deforms such that the cannula 12 can enter into the recess 56. Projections 60 on the arms 54 retain the cannula 12 in the recess 56. The cannula 12 can be released from the clip 50 by flexing the arms 54 outward such that the projections 60 are sufficiently far apart to allow the cannula 12 to exit through the opening 58. If the cannula is flexible and resilient, it can be squeezed to slide past projections 60 for insertion into or removal from the clip 50, after which the cannula resiliently expands to its normal shape.

Figure 4A:
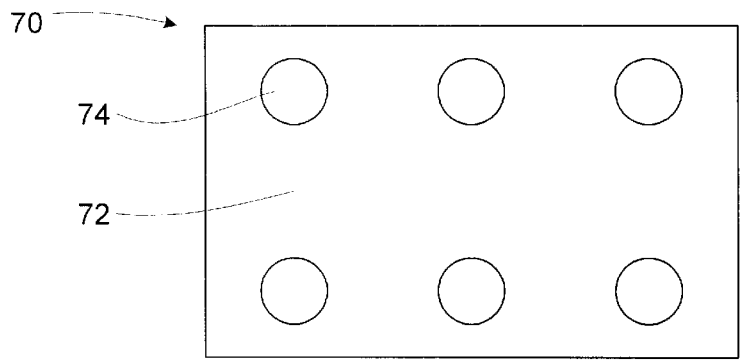
FIGS. 4A and 4B are plan and side views, respectively, of a snap-in clip with protrusions which may be used for gripping a nasal cannula as part of the retainer of the present invention.
Figure 4B:
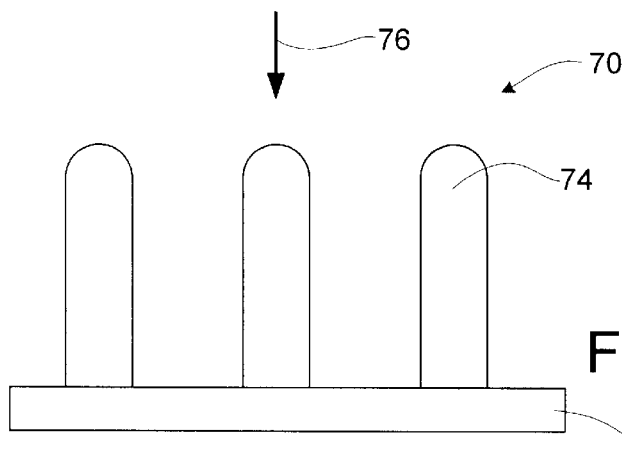
Figure 4C:
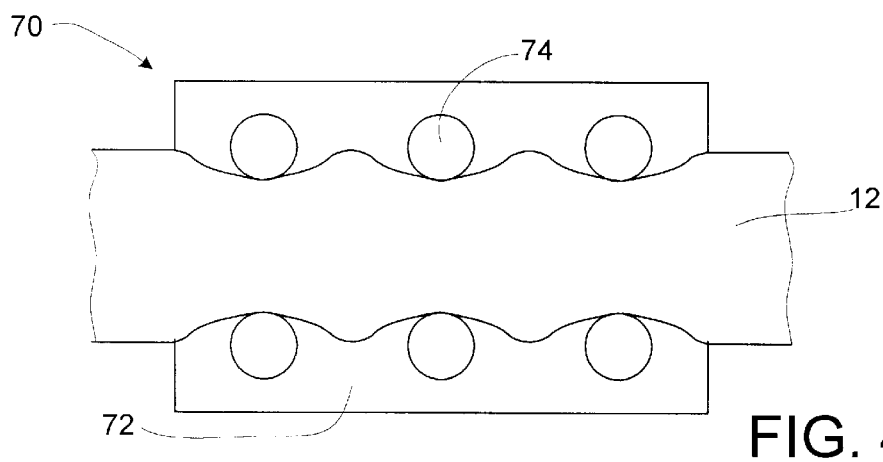
FIG. 4C is a top plan view of the clip of FIGS. 4A and 4B showing a nasal cannula retained in position therein.

FIGS. 4A, 4B and 4C show an alternative embodiment of grip in the form of a clip 70. The clip 70 has a base 72 and protrusions, bumps, legs or posts 74, which are arranged in a pair of rows (preferably parallel rows) and are attached to the base 72. The clip 70 may be of rigid material or resilient material. For example, the clip 70 may be a molded plastic device or a rubber device. The cannula 12 is pressed down onto the clip 70 along direction 76, between the two rows of protrusions, which may provide an interference fit for the cannula 12. The protrusions 74 may be relatively stiff or rigid, and in such case the cannula 12 resiliently deforms slightly where it is compressed between respective protrusions, for example, as is illustrated schematically in FIG. 4C; and friction between the cannula and protrusions holds the cannula in the clip 70. Alternatively, the protrusions 74 may be resilient, and, thus, they move apart to permit the cannula 12 to enter and then to lock the cannula 12 in place after it snaps into place between respective rows of protrusions.

Figure 4D:
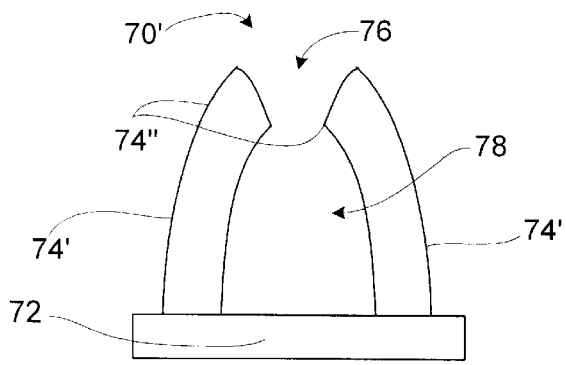
FIG. 4D is an end view of a grip similar to that shown in FIGS. 4A–4C but with curved protrusions.

As another alternative, clip 70' shown in FIG. 4D (primed and double primed reference numerals designate parts that are similar to those designated by the corresponding unprimed reference numeral) has curved protrusions 74'. In such case the cannula 12 is pressed through the area 76 between respective opposite pairs of protrusions 74' into the area 78 of the clip 70'. The area 76 is narrower than the width or outside diameter of the cannula 12. Therefore, either the protrusions 74' or the cannula 12 or both deform(s) to allow the cannula to be pressed past the area 76 into the area 78 for retention therein. The curved distal ends 74" of the protrusions 74' retain the cannula 12 in the area 78 of the clip 70', and interference fit of the cannula 12 with protrusions 74', e.g., as in FIG. 4C, also may hold the cannula in the clip 70'.

Figure 5:
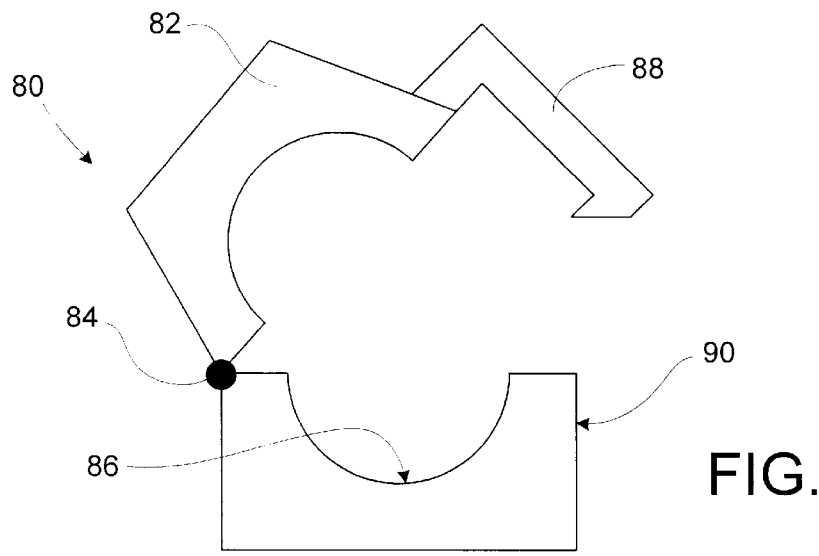
FIG. 5 is a side view of a releasable clamp type clip which may be used for gripping a nasal cannula as part of the retainer of the present invention.

FIG. 5 shows another embodiment of grip 34, a hinged clamp 80. The clamp 80 consists of two halves 82 hingedly connected at a hinge point 84, such as a hinge pin, a flexible hinge, integral molded hinge as part of the halves 82 or the like. The halves 82 have semicircular inner surfaces 86 that combine when the clamp 80 is closed to secure the cannula 12 between the halves 82. The clamp 80 has a releasable locking mechanism, such as the mechanism shown in FIG. 5 as including a pair of releasable interlocking hooks 88, 90, the hook 88 made of a resilient material such that it can resiliently deform, slide past and grab on to the hook 90.

Figure 6:
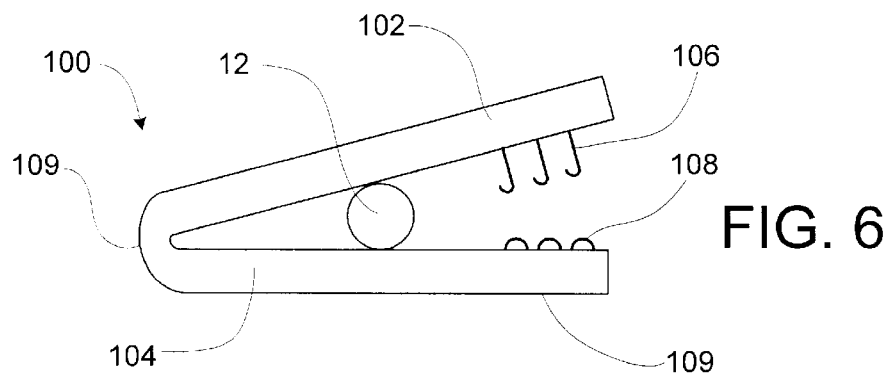
FIG. 6 is a side view of a clip formed of a folded strip of synthetic material having adhering hooks and loops at respective ends, which may be used for gripping a nasal cannula as part of the retainer of the present invention.

FIG. 6 shows another embodiment of grip in the form of a clamping device 100 which includes a strip or strips 102, 104 made of synthetic material with separable adhering hooks 106 and loops 108, such as the material sold under the trademark VELCRO. The clamping device 100 shown in FIG. 6 traps and secures the cannula 12 between the strip of material 102, which has hooks 106, and the other of the strip 104 which has loops 108 or fluffy material, which cooperate with the hooks to hold the strips 102, 104 together. One of the strips 102 may have an adhesive backing 109 for adhering to the flexible member 22, or some other means may be used for such purpose. As is illustrated in FIG. 6, the strips 102, 104 are a single piece of material which is folded at 109, e.g., the fold serves as a hinge, and the hooks 106 and loops 108 are at respective distal ends of the material. Alternatively, the strips 102, 104 may be separate and each may have hooks and loops respectively at opposite ends to cooperate with those on the other strip to hold the two strips together to retain the cannula 12 therebetween, e.g., as is depicted in FIG. 7 described below.

Figure 7:
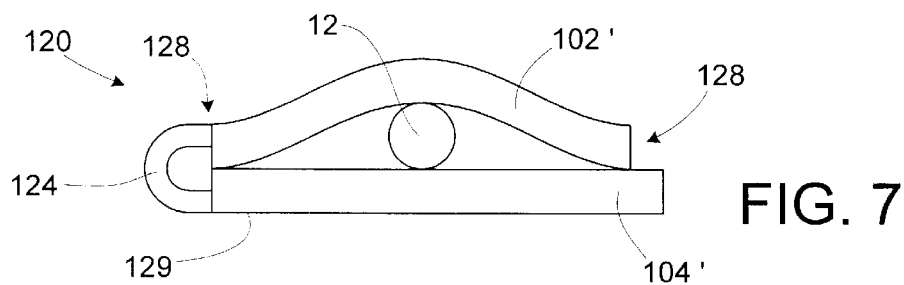
FIG. 7 is a side view of a clip formed by a pair of strips of synthetic material respectively having adhering hooks and loops, which may be used for gripping a nasal cannula as part of the retainer of the present invention.

Another grip in the form of a clamping device 120 shown in FIG. 7 is similar to the device 100 of FIG. 6. The device 120 has strips 102', 104' which are connected by a connecting section 124, thereby preventing loss of one of the strips from the other when they are not adhered. One of the strips or layers 102', 104' may have an adhesive backing 129 for adhering to the flexible member 22. The strips 102', 104' also may have VELCRO or VELCRO type material 130 separably adhering together both ends of both strips 102', 104' on both sides of the cannula 12 as shown, thus holding the cannula to the retainer 22.

Figure 8:
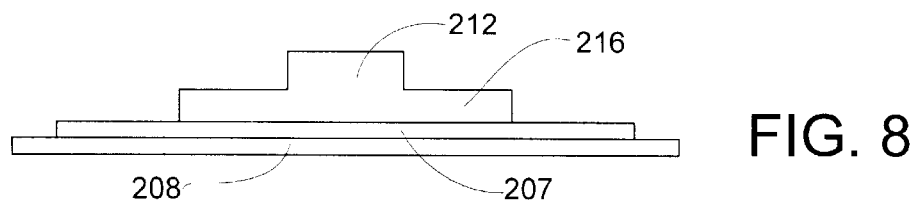
FIG. 8 is a side elevation schematic view of a portion of a nasal cannula retainer according to an embodiment of the invention showing placement of a clip thereof.

FIG. 8 is a schematic illustration of an exemplary technique for the integral formation of the grip 212 to the cheek portion 216 as a single unit. The grip 212 and the cheek portion 216 may be formed as a single unit, for example, by molding, by heat treating, or by adding additional hardener in the vicinity of the grip 212 as the member 202 is formed. The grip 212 is shown schematically and it is representative of the several exemplary grips described and illustrated herein and/or of other grips which provide the function of holding the cannula 12 to the retainer 10.

Thus the present invention provides a means for releasably retaining a nasal cannula by securing the cannula with grips attached to the cheeks of a patient via an adhesive-backed flexible member. The use of releasable and reusable grips allows the cannula to be repositioned or temporarily removed without replacing the retainer or using tape to attach the cannula to the retainer. The retainer thus is able to achieve a long service life while securely attaching the cannula to the patient.

What has been described above are preferred embodiments of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such equivalents, alterations, modifications and variations that fall within the spirit and scope of the appended claims.

What is claimed is:

1. A nasal cannula retainer comprising:

a flexible member for adhering to a patient; and a pair of releasable and reusable grips attached to the flexible member for securing a nasal cannula on opposite sides of a nose of a patient;

wherein the flexible member has a central nose portion configured to be in contact with the nose, and a pair of cheek portions with adhesive backing for adhering to cheeks of the patient, wherein the grips are attached to the cheek portions, and wherein the grips are snap-in clips made of a resilient material.

2. The retainer of claim 1 wherein the clips have a cross-section with a generally semi-circular recess therein conforming to the cannula.

3. The retainer of claim 1 wherein each of the clips include a base and protrusions attached to the base.

4. The retainer of claim 2 wherein each of the clips includes a base and a pair of arms extending from the base.

5. The retainer of claim 4 wherein the base and the arms of each of the clips are a single plastic piece.

6. The retainer of claim 4 wherein each of the arms has a projection thereupon useable for retaining the cannula.

7. The retainer of claim 1 wherein the clips have a cross-section with a generally semi-circular recess therein conforming to a cannula.

8. The retainer of claim 7 wherein each of the clips includes a base and a pair of arms extending from the base.

9. The retainer of claim 8 wherein the base and the arms of each of the clips are a single plastic piece.

10. The retainer of claim 8 wherein each of the arms has a projection thereupon useable for retaining the cannula.

11. The retainer of claim 1 wherein the central nose portion has adhesive backing for adhering to the nose.

12. A method of releasably retaining a nasal cannula, comprising the steps of:

adhering a nasal cannula retainer having a pair of releasable and reusable grips to a patient such that the grips are on opposite sides of a nose of the patient, the adhering including removing a peel layer which covers an adhesive backing of a cheek portion of the retainer, positioning the retainer over the nose, and pressing the adhesive backing against cheeks of the patient;

securing the nasal cannula with the grips at the cheek portions; and wherein the grips are snap-in clips made of a resilient material, and the step of securing includes snapping the cannula into the clips.

13. A method of releasably retaining a nasal cannula, comprising the steps of:

adhering a nasal cannula retainer having a pair of releasable and reusable adhesiveless grips to a patient such that the grips are at cheek portions of the retainer on opposite sides of and distal to a nose of the patient;

securing the nasal cannula with the grips; and wherein the grips are snap-in clips made of a resilient material, and the step of securing includes snapping the cannula into the clips.

\* \* \* \* \*